United States Patent
Goldberg

(12)
(10) Patent No.: US 6,641,799 B2
(45) Date of Patent: Nov. 4, 2003

(54) NASAL SPRAY FOR DECONGESTING NASAL PASSAGES

(75) Inventor: Trevor Ian Goldberg, Charlotte, NC (US)

(73) Assignee: Nos Spray, Inc., Winter Park, FL (US)

( * ) Notice: Subject to any disclaimer, the term of this patent is extended or adjusted under 35 U.S.C. 154(b) by 0 days.

(21) Appl. No.: 10/115,850

(22) Filed: Apr. 3, 2002

(65) Prior Publication Data

US 2003/0190288 A1 Oct. 9, 2003

(51) Int. Cl.[7] .......................... A61K 9/12; A61K 33/18
(52) U.S. Cl. .......................... 424/45; 424/434; 424/51; 514/853
(58) Field of Search .......................... 424/45, 434, 51; 514/853

(56) References Cited

U.S. PATENT DOCUMENTS

| | | |
|---|---|---|
| 4,885,305 A | 12/1989 | Kiechel et al. |
| 4,940,728 A | 7/1990 | Postley |
| 5,164,194 A | 11/1992 | Hettche |
| 5,169,849 A | 12/1992 | Kiechel et al. |
| 5,451,569 A | 9/1995 | Wong et al. |
| 5,498,598 A | 3/1996 | Harris |
| 5,508,282 A | 4/1996 | Tulin-Silver et al. |
| 5,603,935 A | 2/1997 | Jian et al. |
| 5,693,608 A | 12/1997 | Bechgaard et al. |
| 5,840,278 A | 11/1998 | Coleman |
| 5,854,269 A | 12/1998 | Haslwanter et al. |
| 5,897,858 A | 4/1999 | Haslwanter et al. |
| 5,897,872 A | 4/1999 | Picciano |
| 5,898,037 A | 4/1999 | Marx |
| 5,948,414 A | 9/1999 | Wiersma |
| 5,976,573 A | 11/1999 | Kim |
| 5,977,184 A | 11/1999 | Birdsall et al. |
| 6,004,560 A | 12/1999 | Hsu et al. |
| 6,103,218 A | 8/2000 | Brucker et al. |
| 6,143,329 A | 11/2000 | Kim |
| 6,171,611 B1 | 1/2001 | Picciano |
| 6,180,663 B1 | 1/2001 | Lang |
| 6,344,210 B2 | 2/2002 | Fust |
| 2002/0006961 A1 | 1/2002 | Katz et al. |

FOREIGN PATENT DOCUMENTS

WO  WO 194/05330  8/1993

*Primary Examiner*—Michael G. Hartley
*Assistant Examiner*—Mina Haghighatian
(74) *Attorney, Agent, or Firm*—Summa & Allan, P.A.

(57) ABSTRACT

A therapeutic composition for use as a nasal spray the aids in decongesting of the nasal passages by osmotic effect, thinning of mucus and stimulation of ciliary function. Preferred embodiments of the composition contain a sugar solution, a sodium bicarbonate solution, saline, glycerin, water, and a preservative.

46 Claims, No Drawings

NASAL SPRAY FOR DECONGESTING NASAL PASSAGES

FIELD OF THE INVENTION

The present invention relates to therapeutic compositions for treating nasal passages. In particular, the present invention relates to decongesting and moisturizing the tissues that line nasal passages.

BACKGROUND

The nose is a very specialized and complicated structure that serves dual functions as the organ for the sense of smell and as an entry to the respiratory tract. As part of the respiratory tract, a healthy nose moisturizes and warms incoming air and filters out foreign materials.

Nasal passages and other portions of the respiratory tract are lined with specialized tissue layers. In the nose and sinus areas this tissue is often called the nasal mucosa. Like many tissues, the nasal mucosa is composed of several cell layers and cell types. Mucous cells are one type of cell found in the nasal mucosa. These cells are found throughout the nasal mucosa and are generally clustered into small glands. These glands secrete a sticky substance called mucus. Mucus is composed of water, shed epithelial (surface) cells, dead leukocytes, mucin, and inorganic salts, among other things, that are all held in suspension. Mucus functions as a trap for airborne particles (e.g., dust, bacteria, and viruses) that enter the nasal passages. Mucus also lubricates the walls of the nose, sinuses, and throat.

In a healthy nose, the mucus is cleared from the nasal passages on a regular basis by a layer of cells in the nasal mucosa called the ciliated columnar epithelium. These cells possess small hair-like projections called cilia that undulate and "sweep" mucus through the nasal passages allowing it to drain to the back of the throat where it can be swallowed or expelled. This line of defense protects the body against the bacteria and viruses that continually enter the nose and mouth.

Connected to the nose are sinuses or air-filled cavities located behind certain facial bones. There are four groups of sinuses, namely, frontal, sphenoidal, ethmoidal, and maxillary. The sinuses are also lined with mucus secreting tissue. The sinuses are normally kept clear when mucus drains through them into the nasal passages. If they are obstructed for any reason, such as from the congestion present during a cold, normal drainage may not occur and infection of the sinuses may result.

Virtually all persons are occasionally stricken with acute upper respiratory infections (common colds), acute or chronic allergy flare-ups of the nose, and/or acute or chronic non-allergic rhinosinusitis. Persons afflicted by such conditions usually incur significant discomfort and inconvenience.

All of these disorders are characterized by intense inflammation of the nasal mucosa. A number of symptoms contribute to the discomfort and inconvenience associated with the common cold or sinusitis. Symptoms often include one or more of the following: nasal congestion, post-nasal drip, decreased sense of smell, ear fullness, headache, sore throat, malaise, muscle and joint aches, fatigue, cough, chest congestion, fever, chills and gastrointestinal maladies. Considerable research has been conducted over the years aimed at reducing the incidence and duration of symptoms associated with allergies and common colds.

Perhaps the most common symptom experienced by cold and allergy sufferers is "congestion." The term "congestion" is commonly used by the layperson and in the patent literature as catch-all term to describe a complex series of events that hinder a person's ability to breathe through the nose when they have a cold, sinusitis or an allergic reaction.

For example, "congestion" can include a physiological response to an irritant that involves increased blood flow to tissues lining the nose. This increased blood flow causes these tissues to swell and physically block the nasal passages. Alternatively, when a nose is irritated or injured, fluid can seep into the free spaces in the tissues of the nose or build up in individual cells thereby causing additional "congestion". "Congestion" can also include the overproduction of mucus or the buildup of mucus due to increased mucus viscosity or depressed cilia activity or both. "Congestion" may also occur when a person lies on his or her side causing receptor cells in the nose to close off one nasal airway. Changes in temperature and/or humidity can alter the tissue of the nose and cause a "congested" feeling.

Current medications and treatments for "congestion" provide only minimal symptom relief and some have undesirable side effects. Over-the-counter medications containing antihistamines sometimes cause drowsiness and impair cognitive judgment so that driving an automobile or operating other power driven machinery can be dangerous. Decongestants and adrenalin derivatives can elevate blood pressure, cause heart palpitations and stimulate brain activity causing insomnia or hyperalertness.

Numerous over-the-counter sprays (e.g., Afrin®) relieve some symptoms, but contain active ingredients such as the vasoconstrictor oxymetazoline hydrochoride. These types of sprays are directed at reducing swelling caused by increased blood flow to the nasal mucosa and are quite effective. Unfortunately, they are also associated with a significant addictive, rebound phenomenon of the nasal membranes (Rhinitis Medicamentosa). As a result, over-the-counter sprays with these types of active ingredients may actually lengthen the duration of common cold or sinusitis symptoms.

Inhaled corticosteroid nasal sprays provide some relief for allergic rhinitis but do not reduce inflammation caused by acute viral infections, or inflammation associated with other forms of non-allergic rhinitis (atrophic rhinitis, vasomotor rhinitis, hormonally-induced vasomotor instability, etc.). Prolonged use of steroid sprays has also been associated with drying, cracking and bleeding of the nose.

More passive treatments such as isotonic saline mists are also widely marketed for purposes of moisturizing the nose and relieving cold and allergy symptoms. Several patents discuss herbal based mists as an alternative to over-the-counter sprays such as Afrin®.

These more passive sprays and treatments have proved to be less than satisfactory at providing the relief sought by sufferers of colds or allergies or other nasal problems. For example, isotonic saline mists add moisture to the nose but provide little overall relief for congestion.

Accordingly, a need exists for a nasal spray that provides a noticeable measure of relief for those that suffer from "congestion" of the nasal passages yet does not exhibit the harmful side effects associated with sprays that contain active ingredients such as vasoconstrictors and steroids. Such a spray should be economical to produce and safe for use by most individuals suffering from "congestion."

OBJECT AND SUMMARY OF THE INVENTION

In view of the foregoing discussion, an object of the invention is to provide a nasal spray that eases congestion of the nasal passages, in particular, congestion due to decreased ciliary function, swelling, fluid retention, increased mucus secretion and/or mucus buildup.

A further object of the invention is to provide a method for manufacturing such a nasal spray. A still further object of the invention is to provide method of treating the nasal passages, in particular the nasal mucosa, to ease the discomfort associated with congestion due to decreased ciliary function, swelling, fluid retention, increased mucus secretion and/or mucus buildup.

The invention meets these and other objects by providing a composition for osmotic decongestion and moisturization of the nasal passages comprising water, a ciliary stimulant, a mucus thinning agent, an osmotic agent, glycerin, and a preservative. Preferably the composition is alkaline and is hypertonic with respect to the cells of the nasal mucosa.

The invention also meets the above stated objects by providing a method of preparing an alkaline, hypertonic composition for use in osmotic decongestion of the nasal passages. The method comprises obtaining a quantity of water that is between about 67% and 68% of the total composition by volume; adding a quantity of a ciliary stimulant that is between about 4% and 5% of the total composition by volume; adding a quantity of a mucus thinning agent that is about 20% of the total composition by volume; adding a quantity of an osmotic agent that is between about 3% and 4% of the total composition by volume; adding a quantity of glycerin that is about 5% of the total composition by volume; adding less than 1% by volume of a preservative; and stirring the composition to ensure thorough mixing. The method may also comprise adjusting the pH of the composition to between 7.5 and 8.5 and packaging the composition for use as a nasal spray by individuals.

The invention also provides a method of relieving congestion of the nasal mucosa consisting of removing fluid from the nasal mucosa through osmosis by the application of a hypertonic solution comprising sugar, thinning the mucus present in the nose by the application of an alkaline solution; and stimulating ciliary function by application of a saline solution wherein the steps of removing fluid, thinning mucus and stimulating ciliary function are all physiological responses to the application of a single hypertonic, alkaline composition comprising a sugar solution, an alkaline solution and a saline solution.

DETAILED DESCRIPTION

As mentioned previously, the term "congestion" is often used to describe a combination of physiological responses that result in clogged nasal passages and sinuses. Many of the known nasal sprays concentrate on the reduction of blood flow to the nasal mucosa through use of vasoconstrictors. These sprays are typically formulated to maximize the benefit of the vasoconstrictors and provide little or no therapeutic action in regard to the other causes of nasal congestion. Other, more passive sprays, lubricate or moisten the nose but provide little relief in the way of decongestion.

In contrast, the present invention is a hypertonic, alkaline nasal spray that avoids the use of vasoconstrictors and aids in the decongesting and moisturizing of the nose through osmotic activity, thinning and decreasing the viscosity of mucus, and increasing ciliary function.

For purposes of this discussion, osmosis may be defined as the spontaneous passage or diffusion of water through a semipermeable membrane (one that blocks the passage of dissolved substances) from an area of higher water concentration to an area of lower water concentration. Stated alternatively, water will diffuse down its concentration gradient or into a hypertonic environment to achieve a state of equilibrium. The semipermeable membranes at issue here are the tissues of the nasal mucosa and even the plasma membranes of individual cells within the tissues.

In one embodiment, the spray according to the invention is a composition for inducing osmotic decongestion of nasal passages. The composition also lubricates and moisturizes the nose and thins mucus. The composition is comprised primarily of water and other passive components.

One component of the composition is a ciliary stimulant. As noted previously, the action of cilia in cells of the nasal mucosa is important in keeping the nasal passages clear of mucus. If cilia function is subnormal, mucus will build up and contribute to congestion of the nasal passages.

Saline solutions provide a physiological stimulant for ciliary activity. Saline solutions are relatively inexpensive and are simple to prepare. Accordingly, in a preferred embodiment of the invention the ciliary stimulant is a saline solution that is between 23% and 24% sodium chloride (i.e., 23 mg NaCl/ml water). In a more preferred embodiment the saline solution is a 23.4% solution of sodium chloride.

Another component of the composition according to the invention is a mucus thinning agent. As used herein, the term mucus thinning agent is defined as an agent, other than water, that lowers the viscosity of the mucus thereby making it more susceptible to transport by the cilia. For example, mucus derives its name from the substance mucin, which is secreted as part of the mucus. Mucins are high molecular weight glycoproteins with an oily texture that provide protection and lubricating functions. Mucin is a fairly viscous substance and adds to the viscosity of mucus. The viscosity of mucin, and in turn that of mucus, can be altered by a change in pH. The higher the pH, the less viscous the mucin.

Accordingly, in preferred embodiments the mucus thinning agent utilized in the practice of the invention is an alkaline agent, in particular, an about 8% to about 9% solution of sodium bicarbonate and water (e.g., 8 mg $NaHCO_3$/ml water). In more preferred embodiments the sodium bicarbonate solution is about 8.4%.

As noted above, the composition according to the invention uses osmosis to aid in the decongestion of the nasal passages. In general terms, the osmotic effect utilized in the present invention can be described as follows: by bathing the nasal mucosa in a hypertonic solution, osmotic forces will drive (or pull) water from the free spaces in the nasal mucosa tissue and from the intracellular environment into the nasal passages thereby shrinking the nasal mucosa and providing extra fluid for moisturizing the nose and transportation of the mucus from the nasal passages.

This osmotic effect requires that the composition be hypertonic with respect to the nasal mucosa. Although all of the components present in the composition contribute to the hypertonicity of the composition, as used herein the term osmotic agent refers to an agent specifically added to the composition to increase the solute level in the composition and contribute to achieving hypertonicity of the spray. In preferred embodiments the osmotic agent used in the practice of the invention is a sugar selected from the group comprising monosaccharides and disaccharides. Sugars such as glucose, sucrose and fructose are preferred with sucrose being especially preferred.

The osmotic agent utilized in the practice of the invention is preferably an 85% solution of a sugar, preferably sucrose, and water.

Another aspect of the invention is to increase the moisture and lubrication inside the nose. During colds or allergic responses, the inside of the nose can become irritated and dry due to natural forces or in response to medications. Some people naturally have a dry nose which can lead to cracking and scaling within the nose. The composition according to the invention addresses these issues by including glycerin as a moisturizer and lubricant. The glycerin also aids in achieving the hypertonic nature of the composition. Preferably the glycerin is U.S.P. grade (99.5%).

As noted previously, the composition preferably has an alkaline pH to lower the viscosity of mucus. In preferred embodiments the pH of the composition is between about 7.5 and 8.5, most preferably around 8. The incorporation of the above discussed mucus thinning agent will usually ensure that the composition is alkaline in nature. If downward pH adjustment is required the addition of small amounts of an acid can be used to achieve a pH of about 8. Any physiological acceptable acid may be used. A 10% hydrochloric acid solution has been used in test samples and provides acceptable results. In the unlikely event upward pH adjustment is necessary, additional sodium bicarbonate may be used.

A preservative should also be used to maintain the integrity of the composition. Suitable preservatives are well known to those skilled in the art. In preferred embodiments, however, a small quantity (e.g., less than 1% by volume) of potassium sorbate is added to the composition.

The preferred relative amounts of each of the above components in the total composition can be summarized as follows: between about 67% and 68% water; between about 4% and 5% of the ciliary stimulant; between about 3% and 4% of the osmotic agent; about 5% glycerin; about 20% of the mucus thinning agent; less than 1% of a preservative; and a small quantity of a pH adjusting agent if needed.

The composition according to the invention is most efficiently made in stepwise fashion by adding and mixing the components with sterile water. In a preferred embodiment the method comprises preparing a composition that is between about 67% and 68% water and adding to the water a 23% to 24% saline solution that is between about 4% and 5% of the total composition by volume. To this is added a quantity of an 85% sugar solution that equals between about 3% and 4% of the total composition by volume.

The method further comprises adding a quantity of glycerin such that it is about 5% of the total composition by volume.

Next, a quantity of 8% to 9% sodium bicarbonate solution is added such that the quantity is about 20% of the total composition by volume.

Lastly, add about 1 ml of a 100 mg/ml potassium sorbate U.S.P. solution and mix thoroughly. Small amounts of 10% hydrochloric acid or additional sodium bicarbonate may be added to achieve a pH of between about 7.5 and 8.5.

Those skilled in the art recognize that the particular order of mixing the recited components is not critical to the practice of the invention. Accordingly, to the extent the invention is described herein as a series of steps, the order of those steps should not be interpreted as limiting the scope of the invention.

Example for Compounding 1000 ml of Composition

1. Prepare or obtain a 23.4% sodium chloride solution (234 mg/ml). For 1000 ml of composition use about 10,132 mg of sodium chloride which is approximately 43.3 ml of the 23.4% solution.

2. Prepare or obtain an 8.4% sodium bicarbonate solution (84 mg/ml). For 1000 ml of composition use about 16,800 mg of sodium bicarbonate which is approximately 200 ml of the 8.4% solution.

3. Prepare or obtain a simple syrup solution that is approximately 85% sucrose. For 1000 ml of composition use about 33.3 ml of the simple syrup solution.

4. Obtain 50 ml of glycerin U.S.P. (99.5%).

5. Prepare or obtain a solution of potassium sorbate U.S.P. For 1000 ml of composition, use about 0.1% which is 100 mg/1000 solution. The potassium sorbate solution can be prepared by weighing 1000 mg and transferring it to a beaker. To this add a small amount of sterile water to dissolve the entire amount of potassium sorbate. Using a small syringe (e.g., 12 cc) draw the solution out of the beaker and quantity sufficient the volume up to 10 ml. This produces a concentrate solution of 100 mg/ml.

Example for Preparing Nasal Spray

Using the above components, the osmotic nasal decongestion according to the invention may then be prepared into a spray in the following manner, preferably under a laminar hood.

1. Add 21.65 ml of the sodium chloride solution into two 500 ml beakers.

2. Add 100 ml of the sodium bicarbonate solution into each of the two 500 ml beakers.

3. Add 16.65 ml of the simple syrup solution into each of the two 500 ml beakers.

4. Add 25 ml of glycerin into each of the two 500 ml beakers.

5. Stir each beaker with a glass stirring rod for uniformity.

6. Add 336.7 ml of sterile water into each of the two 500 ml beakers.

7. Stir each beaker with a glass stirring rod for uniformity.

8. Add 50 mg (0.5 ml) of potassium sorbate to each beaker using a 1.5 micron filter, stirring each beaker well after addition.

9. Check pH of each beaker with universal litmus paper. Adjust to about 8 pH if needed by adding a 10% hydrochloric acid solution in a dropwise fashion.

10. Transfer the contents of each beaker into a number of commereially available atomizer units for use by an individual. Transfer about 28 ml per unit.

In a further embodiment, the invention comprises a method of moisturizing and relieving nasal congestion comprising applying a composition to the nasal mucosa where the composition comprises: about 67% to 68% water with the remainder of the composition comprising a ciliary stimulant, a mucus thinning agent, an osmotic agent, glycerin, a pH adjusting agent (if needed), and a preservative where each of the above components are present in the amounts discussed previously.

That which is claimed is:

1. A composition for osmotic decongestion and moisturization of the nasal passages consisting essentially of:
   water;
   a ciliary stimulant that is an about 23% to about 24% saline and is between about 4% and 5% of the total composition by volume;
   a mucus thinning agent;

a sugar solution as an osmotic agent;
glycerin; and
a preservative,
wherein said composition is alkaline and is hypertonic with respect to cells of the nasal mucosa.

2. A composition according to claim 1 wherein said mucus thinning agent is an alkaline agent.

3. A composition according to claim 2 wherein said mucus thinning agent is an alkaline solution that is between about 8% and 9% sodium bicarbonate and is about 20% of the total composition by volume.

4. A composition according to claim 1 further comprising a pH adjusting agent.

5. A composition according to claim 4 wherein said acid is a 10% solution of hydrochloric acid.

6. A composition according to claim 1 wherein the pH of the composition is between about 7.5 and about 8.5.

7. A composition according to claim 6 wherein the pH is about 8.

8. A composition according to claim 1 wherein said sugar is selected from the group consisting of monosaccharides ad disaccharides.

9. A composition according to claim 8 wherein said sugar is selected from the group consisting of glucose, sucrose and fructose.

10. A composition according to claim 9 wherein said sugar is sucrose.

11. A composition according to claim 1 wherein said osmotic agent is an about 85% sucrose solution and is between about 3% and 4% of the total composition by volume.

12. A composition according to claim 1 wherein said preservative is potassium sorbate.

13. A composition according to claim 1 wherein said glycerin is about 5% of the total composition by volume.

14. A composition for osmotic decongestion and lubrication of the nasal passages consisting essentially of:
between 67% and 68% water;
between 4% and 5% of a 23% to 24% saline solution;
between 3% and 4% of an 85% sugar solution;
about 5% glycerin;
about 20% of a 8% to 9% sodium bicarbonate solution; and
a preservative;
wherein said composition has a pH of about 8 and is hypertonic with respect to cells of the nasal mucosa.

15. A composition according to claim 14 wherein said sugar is selected from the group consisting of monosaccharides and disaccharides.

16. A composition according to claim 15 wherein said sugar is selected from the group consisting of glucose, sucrose and fructose.

17. A composition according to claim 14 wherein said sugar is glucose.

18. A composition according to claim 14 wherein said preservative is potassium sorbate.

19. A composition according to claim 14 further comprising hydrochloric acid.

20. A method of preparing an alkaline, hypertonic composition for use in osmotic decongestion of the nasal passages, the method consisting essentially of:
obtaining a quantity of water that is between about 67% and 68% of the total composition by volume;
adding a quantity of a ciliary stimulant that is a saline and is between about 4% and 5% of the total composition by volume;
adding a quantity of a mucus thinning agent that is about 20% of the total composition by volume;
adding a quantity of an osmotic agent that is a sugar solution and is between about 3% and 4% of the total composition by volume;
adding a quantity of glycerin that is about 5% of the total composition by volume;
adding less than 1% by volume of a preservative;
stirring the composition to ensure thorough mixing and adjusting the pH to between 7.5 and 8.5.

21. A method according to claim 20 wherein the ciliary stimulant is an about 23% to about 24% saline solution.

22. A method according to claim 20 wherein the mucus thinning agent is an alkaline agent.

23. A method according to claim 22 wherein the mucus thinning agent is an alkaline solution that is between about 8% and about 9% sodium bicarbonate.

24. A method according to claim 20 wherein the pH adjustment is accomplished by adding a 10% solution of hydrochloric acid.

25. A method according to claim 20 wherein the pH is adjusted to about 8.

26. A method according to claim 20 wherein the sugar is selected from the group consisting of monosaccharides or disaccharides.

27. A method according to claim 26 wherein the sugar is selected from the group consisting of glucose, sucrose and fructose.

28. A method according to claim 27 wherein the sugar is sucrose.

29. A method according to claim 20 wherein the preservative is potassium sorbate.

30. A method according to claim 20 further comprising the step of packaging the composition for use by an individual.

31. A method of moisturizing and relieving congestion of the nasal mucosa consisting of applying to the nasal mucosa a composition consisting essentially of:
about 67% to 68% water;
a ciliary stimulant that is an about 23% to about 24% saline solution and is between about 4% and 5% of the total composition by volume;
a mucus thinning agent;
a sugar solution as an osmotic agent;
glycerin;
a pH adjusting agent; and
a preservative,
wherein said composition is alkaline and hypertonic with respect to cells of the nasal mucosa.

32. A method according to claim 31 wherein the mucus thinning agent is an alkaline agent.

33. A method according to claim 32 wherein said mucus thinning agent is an alkaline solution that is between about 8% and 9% sodium bicarbonate and is about 20% of the total composition by volume.

34. A method according to claim 31 wherein the pH adjusting agent is an acid.

35. A method according to claim 34 wherein the pH adjusting agent is a 10% solution of hydrochloric acid.

36. A method according to claim 31 wherein the pH of the composition is between about 7.5 and about 8.5.

37. A method according to claim 36 wherein the pH of the composition is about 8.

38. A method according to claim 31 wherein the sugar is selected from the group consisting of monosaccharides and disaccharides.

39. A method according to claim 38 wherein the sugar is selected from the group consisting of glucose, sucrose and fructose.

40. A method according to claim 39 the sugar is sucrose.

41. A method according to claim 31 wherein the osmotic agent is an about 85% sucrose solution and is between about 3% and 4% of the total composition by volume.

42. A method according to claim 31 wherein the preservative is potassium sorbate.

43. A method according to claim 31 wherein the glycerin is about 5% of the total volume of the composition.

44. A method of relieving congestion of the nasal mucosa consisting of:

removing fluid from the nasal mucosa through osmosis by the application of a hypertonic solution comprising sugar;

thinning the mucus present in the nose by the application of an alkaline solution; and stimulating ciliary function by application of a saline solution;

wherein the steps of removing fluid, thinning mucus and stimulating ciliary function are all physiological responses to the application of a single composition consisting essentially of water, an alkaline mucus thinning agent, a sugar solution, glycerine, a preservative, an a saline solution.

45. A method according to claim 44 further comprising moistening the nasal mucosa through the application of glycerin to a nasal mucosa.

46. A method according to claim 45 wherein the pH of the combined elements applied to the nasal mucosa is about 8.

* * * * *

UNITED STATES PATENT AND TRADEMARK OFFICE
CERTIFICATE OF CORRECTION

PATENT NO. : 6,641,799 B2  
DATED : November 4, 2003  
INVENTOR(S) : Trevor Ian Goldberg It is certified that error appears in the above-identified patent and that said Letters Patent is hereby corrected as shown below:

Column 6,
Line 65, after "saline" insert -- solution --.

Column 7,
Line 65, after "saline" insert -- solution --.

Column 9,
Line 4, after "39" insert -- wherein --.

Column 10,
Line 10, "an" should read -- and --.
Line 12, "moistening" should read -- moisturizing --.
Line 13, "a" should read -- the --.

Signed and Sealed this

Twenty-seventh Day of April, 2004

JON W. DUDAS  
*Acting Director of the United States Patent and Trademark Office*